(12) United States Patent
Yang et al.

(10) Patent No.: US 7,886,623 B2
(45) Date of Patent: Feb. 15, 2011

(54) NANO-PARTICLE CONTAINING APPARATUS, NANO-PARTICLE DETECTION SYSTEM AND METHOD THEREOF

(75) Inventors: Chung-Shi Yang, Taichung (TW);
Fu-Der Mai, Taoyuan County (TW);
Bega Liu, Hsinchu County (TW);
Jen-Kun Chen, Hsinchu (TW);
Yong-Chien Ling, Hsinchu (TW);
Feng-Yin Li, Taichung (TW)

(73) Assignee: National Health Research Institutes, Miaoli County (TW)

( * ) Notice: Subject to any disclaimer, the term of this patent is extended or adjusted under 35 U.S.C. 154(b) by 658 days.

(21) Appl. No.: 11/859,259

(22) Filed: Sep. 21, 2007

(65) Prior Publication Data

US 2008/0202208 A1 Aug. 28, 2008

Related U.S. Application Data

(60) Provisional application No. 60/826,770, filed on Sep. 25, 2006.

(51) Int. Cl.
*G01N 17/00* (2006.01)

(52) U.S. Cl. .................................... 73/865.6

(58) Field of Classification Search ........................ None
See application file for complete search history.

(56) References Cited

U.S. PATENT DOCUMENTS

| 6,567,157 | B1 * | 5/2003 | Flagan et al. .................. 356/37 |
| 7,064,827 | B2 * | 6/2006 | Nurmikko et al. ........... 356/338 |
| 2004/0045341 | A1 * | 3/2004 | Suzuki et al. ............... 73/28.02 |

* cited by examiner

*Primary Examiner*—Robert R Raevis
(74) *Attorney, Agent, or Firm*—Rosenberg, Klein & Lee

(57) ABSTRACT

A nano-particle containing apparatus, a nano-particle detection system and a method are disclosed. The nano-particle containing apparatus includes a casing, an air extracting device, a pressure device and a measuring instrument. The casing has a containing space for disposing a plurality of nano-particles. An internal wall surface of the casing has active self-cleaning function. The pressure control device controls the pressure status of the containing space. The active self-clean function is that nano-particles adhered to the internal surface wall are removed into the containing space. The nano-particles then are pumped by the air extracting device from the containing space. The measuring instrument then detects the status of an object affected by the nano-particles after the object is delivered into the containing space.

20 Claims, 8 Drawing Sheets

4 mg/mL BSA in 0.2 M ammonium acetate 0.02 mg/mL BSA in 0.2 M ammonium acetate

GNP 5 nm direct #5

NANO-PARTICLE CONTAINING APPARATUS, NANO-PARTICLE DETECTION SYSTEM AND METHOD THEREOF

FIELD OF THE INVENTION

The present invention relates to a nano-particle containing apparatus, a nano-particle detection system and its method, and more particularly to the nano-particle containing apparatus, the nano-particle detection system and the method that detect the effect degree of an object exposed to nano-particles.

BACKGROUND OF THE INVENTION

Since the application of nano-technology is in widespread use, the safety of nano-technology has become more and more important to people, nano-particles especially. Referring to FIG. 1 for the schematic diagram illustrates a conventional nano-particle detection system. An organism 11 is fastened, and the nose of the organism 11 is covered with a pipe of a nano-particle generator 10 to enable nanosuspension particles 12 generated by the nano-particle generator 11 to be inhaled inside the body of the organism 11. The effect degree of the organism 11 exposed to the nanosuspension particles 12 then is detected after taking for a while.

However, the conventional nano-particle detection system may not precisely detect the effect degree of human bodies exposed to nano-particles since it is completely different from the real environment. Moreover, the conventional nano-particle detection system may not perform quantitative experiment either. Consequently, precise data may not be provided for the standard of evaluating safety of nano-particles.

Therefore, the inventor(s) of the present invention based on years of experience on related research and development invents a nano-particle containing apparatus, a nano-particle detection system and its method to overcome the foregoing shortcomings.

SUMMARY OF THE INVENTION

Accordingly, an objective of the present invention is to provide a nano-particle containing apparatus, a nano-particle detection system and method thereof to precisely evaluate the effect degree of an object exposed to the nano-particles.

In accordance with the objective of the present invention, the nano-particle containing apparatus includes a casing, an air extracting device, a pressure control device and a measuring instrument. The casing has a containing space for accommodating a plurality of nano-particles. The air extracting device is provided for pumping the nano-particles from the containing space. The pressure control device is provided for controlling the pressure status of the containing space. The measuring instrument is provided for detecting the status of an object affected by the nano-particles after the object is delivered into the containing space.

Another objective of the present invention is to provide a nano-particle detection system that includes a generating device, a containing apparatus, an analyzer and a detector. The generating device can generate a plurality of nano-particles. The containing apparatus has a containing space that allows the nano-particles to be uniformly distributed therein. The analyzer analyzes particle sizes of the nano-particles within the containing space. The detector can detect a concentration of the nano-particles within the containing space. An object then is placed into the containing space, and the effect degree of the object exposed to the nano-particles then is detected after achieving a predetermined time.

A third objective of the present invention is to provide a method for evaluating safety of nano-particles. The method includes the following steps of: providing a containing space to place an object; injecting a plurality of nano-particles into the containing space to allow the nano-particles to be uniformly distributed inside the containing space; and evaluating the effect degree of the object exposed to the nano-particles after achieving a predetermined time. The object can be a biological specimen or a liquid-like object (colloid).

Other features and advantages of the present invention and variations thereof will become apparent from the following description, drawings, and claims.

DETAILED DESCRIPTION OF THE PREFERRED EMBODIMENTS

Figure 1:
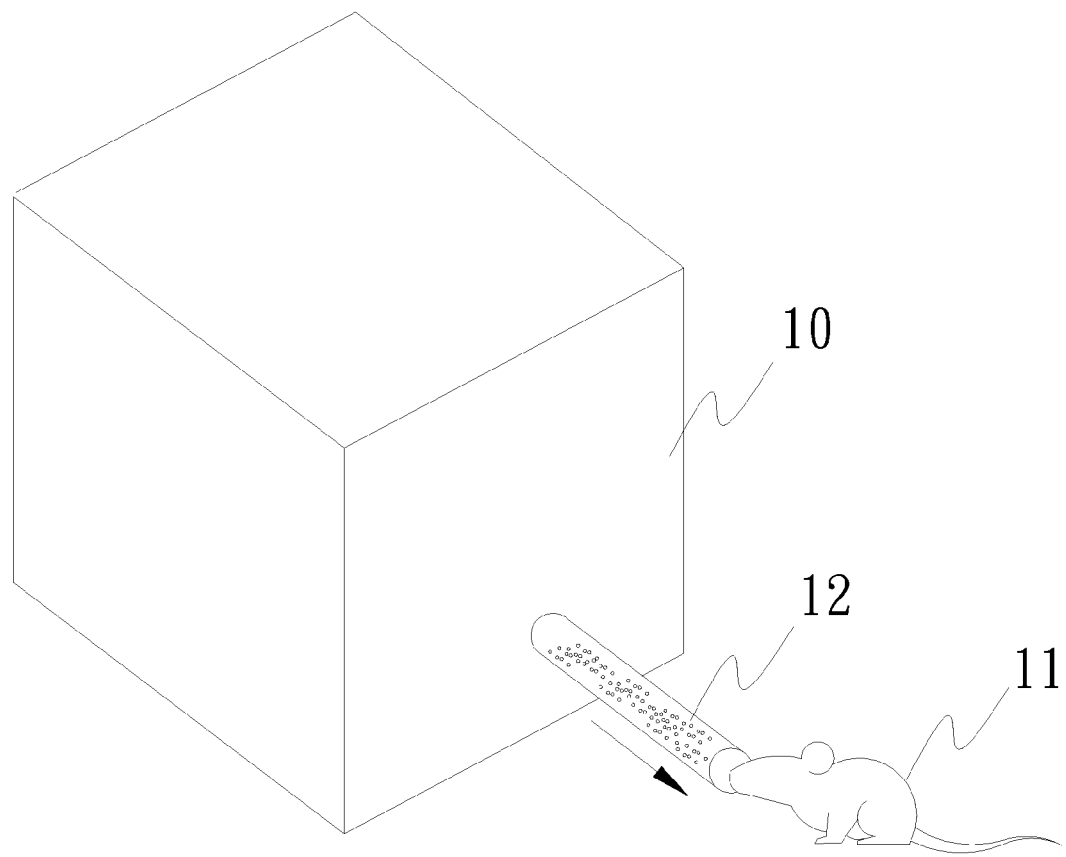
FIG. 1 is a schematic diagram illustrating a conventional nano-particle detection system.
Figure 2:
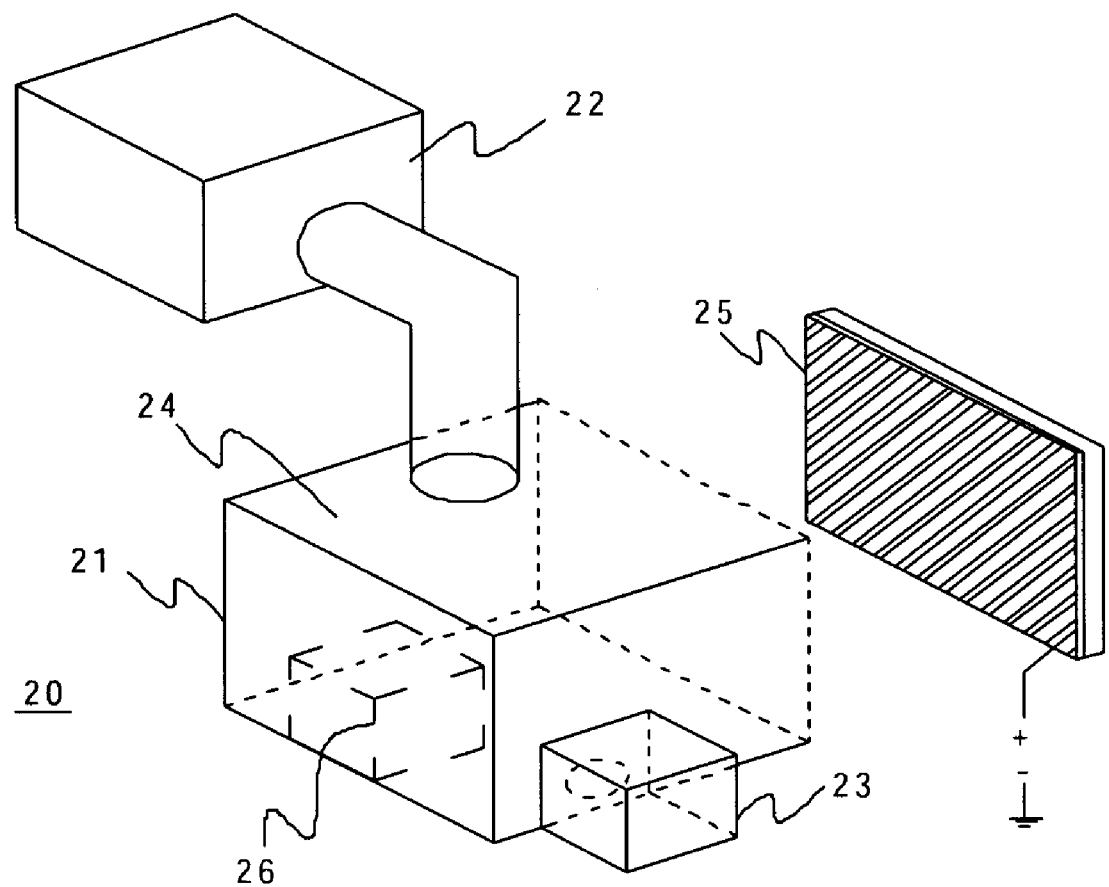
FIG. 2 is a schematic diagram illustrating a nano-particle containing apparatus of the present invention.

Referring to FIG. 2 for the schematic diagram illustrates a nano-particle containing apparatus of the present invention. The nano-particle containing apparatus 20 includes a casing 21, an air extracting device 22, a pressure control device 23 and a measuring instrument 26. The casing 21 has a containing space 24 for accommodating a plurality of nano-particles. An internal wall surface of the casing 21 has active self-cleaning function. The pressure control device 23 is provided for controlling the pressure status of the containing space 24. For example, the pressure control device 23 can control the negative or positive pressure of the containing space 24 to prevent the nano-particles within the containing space 24 from being leaked. Experimenters may not be harmed and environmental pollution may not occur. Since the size of the nano-particles is extremely small and easily attached to the internal wall surface, the nano-particles are removed into the containing space 24 through active self-cleaning function. The air extracting device 22 then pumps the nano-particles from the containing space 24. Afterward, the measuring instrument 26 detects the status of an object (not shown in the figure) affected by the nano-particles after the object is delivered into the containing space 24. It should be noted that the measuring instrument 26 can be disposed inside the casing 21 or outside the casing 21.

Active self-cleaning function can be preferably executed by disposing a conductive thin film 25 to the internal wall surface of the casing 21. According to an electrical property of the nano-particles attached to the internal wall surface, a potential difference corresponding to the electrical property is employed to the conductive thin film 25, and the nano-particles then are removed into the containing space 24 by utilizing the mutual repulsion effect. Moreover, the nano-particle containing apparatus 20 can be repeatedly utilized and different nano-particles can be distributed therein through the aforesaid process.

The air extracting device 22 is preferably a pump such as a vacuum pump. The pressure device 23 is preferably a negative or positive pressure device or an air duct negative pressure device. The measuring instrument further includes a temperature monitoring and control device for monitoring and reading the temperature of the containing space 24, a humidity monitoring and control instrument for monitoring and reading the humidity of the containing space 24 and a carbon dioxide control device for monitoring and reading the concentration of carbon dioxide in the containing space 24.

Figure 3:
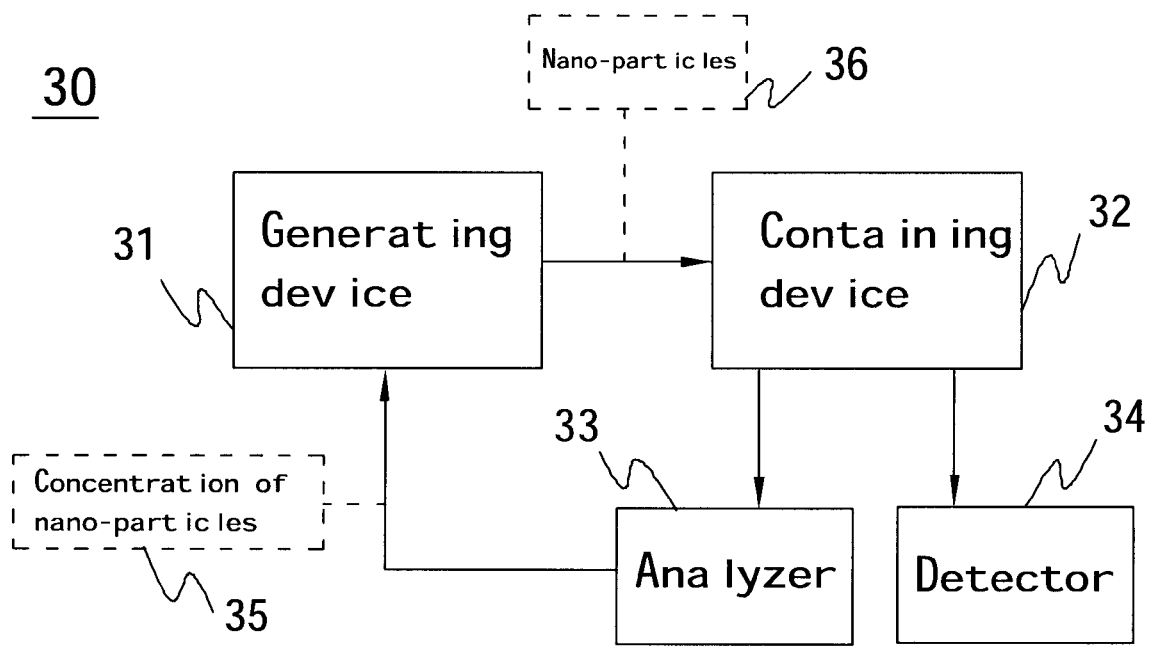
FIG. 3 is a block diagram illustrating a nano-particle detection system of the present invention.

Referring to FIG. 3 for the block diagram illustrates a nano-particle detection system of the present invention. The nano-particle detection system 30 includes a generating device 31, a containing apparatus 32 having a containing space, an analyzer 33 and a detector 34. The generating device 31 is provided for generating a plurality of nano-particles 36 that are injected into the containing space of the containing apparatus 32. The analyzer 33 analyzes particles sizes of the nano-particles 36 within the containing space. The detector 34 detects a concentration 35 of the nano-particles 36 within the containing space. An object then is placed into the containing space, and the effect degree of the object exposed to the nano-particles 36 is detected after achieving a predetermined time.

Figure 4:
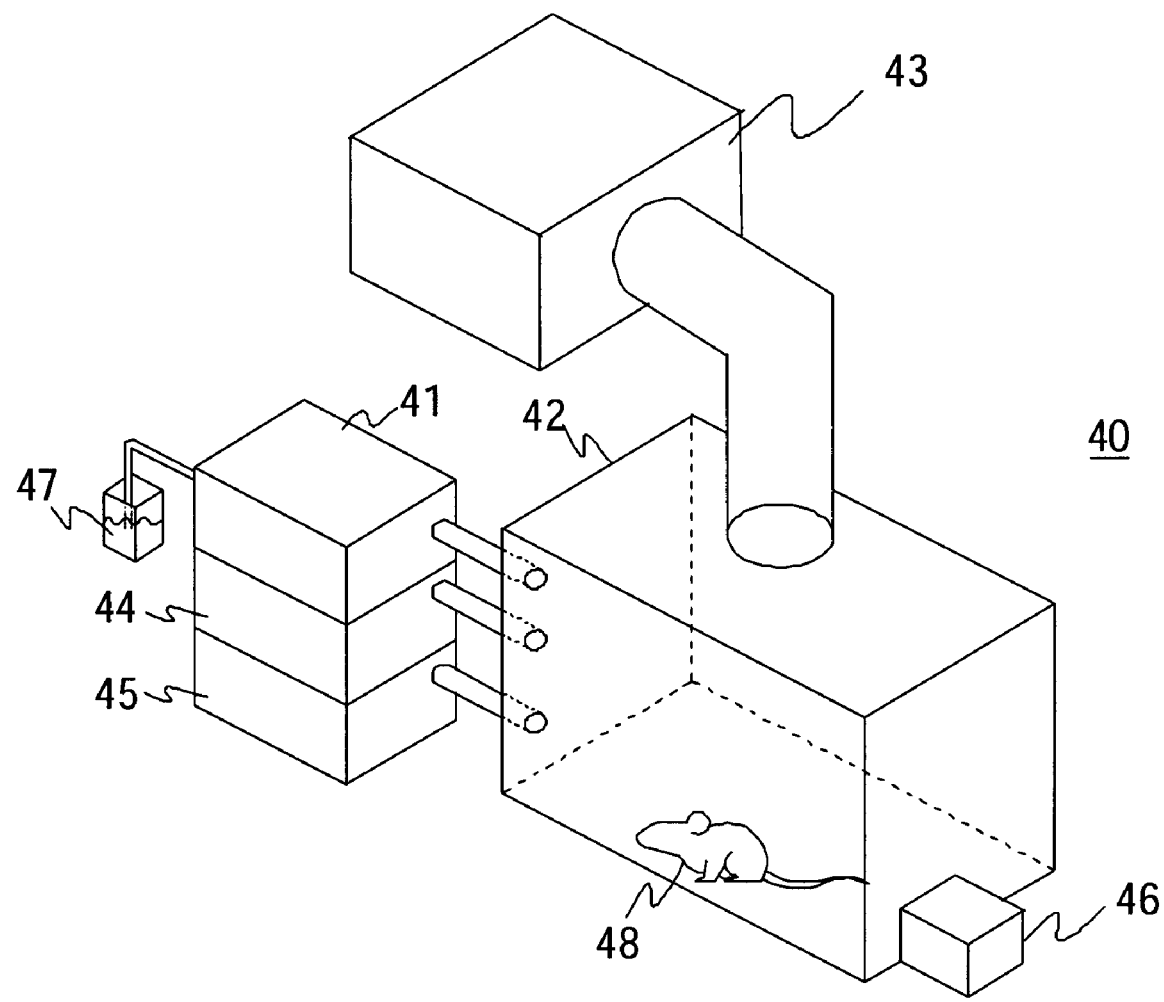
FIG. 4 is a schematic diagram illustrating a nano-particle detection system according to a preferred embodiment of the present invention.

Referring to FIG. 4 for the schematic diagram illustrates a nano-particle detection system according to a preferred embodiment of the present invention. The nano-particle detection system 40 includes pneumatic and spray equipment 41 (or an electronic spray device), a casing 42, a vacuum pump 43, an analyzer 44, a detector 45 and a negative pressure controlling device 46. The pneumatic and spray equipment 41 draws nano-substances 47 in liquid shape through a pipette. Small drops of the nano-substances 47, cleaner air and carbon dioxide then are mixed and neutralized to eliminate charges. The drops then are dry-heated to enable the drops to be vaporized and to become smaller due to heat and dry condition. Nanosuspension particles then are produced and injected into the casing 42. The nanosuspension particles can be uniformly distributed into the casing 42. The detector 44 can detect a concentration of the nanosuspension particles within the casing 42 and control the velocity of generating the nanosuspension particles from the pneumatic and spray equipment 41 based on the concentration data, thereby controlling the concentration of the nanosuspension particles within the casing 42 at a predetermined range. The analyzer 45 can analyze particle size distribution of the nanosuspension particles within the casing 42 and control the pneumatic and spray equipment 41 based on the concentration data, thereby controlling the particle size distribution of the nano-suspension particles within the casing 42 at a predetermined range. Afterward, an object 48 such as a biological specimen or a liquid-like object (colloid) is placed into the casing 42 to allow the object 48 to be exposed to the nanosuspension particles. The effect degree of the object 48 exposed to the nanosuspension particles then is detected after achieving a predetermined time. The negative pressure control device 46 controls the negative pressure status of the casing 42 to prevent the nanosuspension particles from being leaked.

Moreover, the internal wall surface of the casing 42 can have a conductive thin film. When a user would like to test different nano-particles, a potential difference corresponding to the electrical property is imposed to the conductive thin film based on an electrical property of the nano-particles attached to the internal wall surface. The nano-particles then are removed from the internal wall surface by utilizing a mutual repulsion effect, and the vacuum pump 43 is utilized to pump the nano-particles from the casing 42. The nano-particle detection system 40 can repeat the test for different nano-particles through the aforesaid process.

Figure 5:
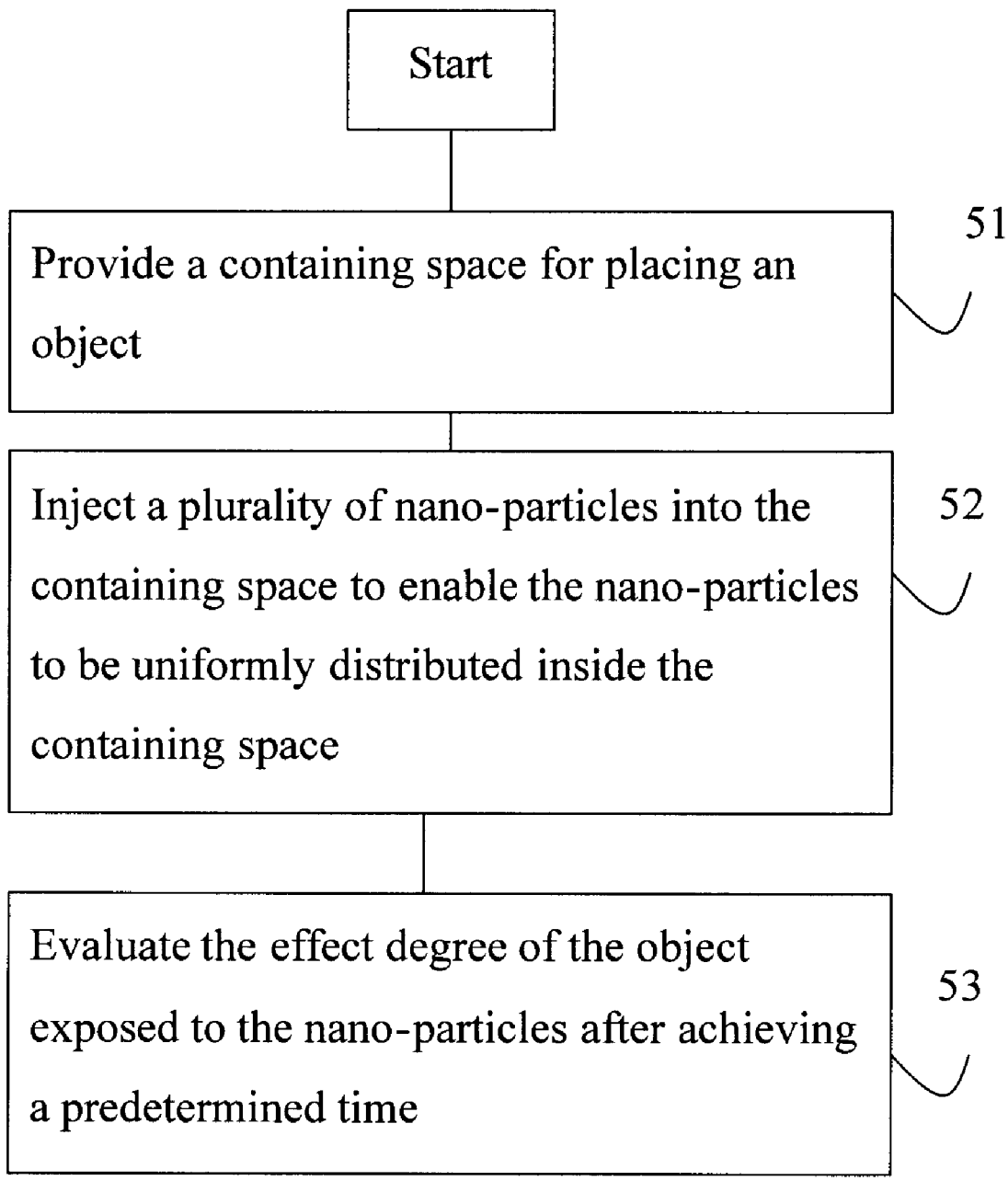
FIG. 5 is a flowchart illustrating a method for evaluating safety of nano-particles of the present invention.

Referring to FIG. 5 for the flowchart illustrates a method for evaluating safety of nano-particles of the present invention. The method comprises the following steps:

Step 51: provide a containing space for placing an object;

Step 52: inject a plurality of nano-particles into the containing space to enable the nano-particles to be uniformly distributed inside the containing space; and Step 53: evaluate the effect degree of the object exposed to the nano-particles after achieving a predetermined time.

Moreover, the method further includes the steps of monitoring and controlling the pressure status, the temperature status, the humidity status and the concentration of carbon dioxide. The object is preferably a biological specimen or a liquid-like object (colloid).

Referring to Table 1 for the specification illustrates the experiment conditions executed by the nano-particle detection system of the present invention. The optimum results can be achieved by actually operating the nano-particle detection system and software simulation.

Figure 6:
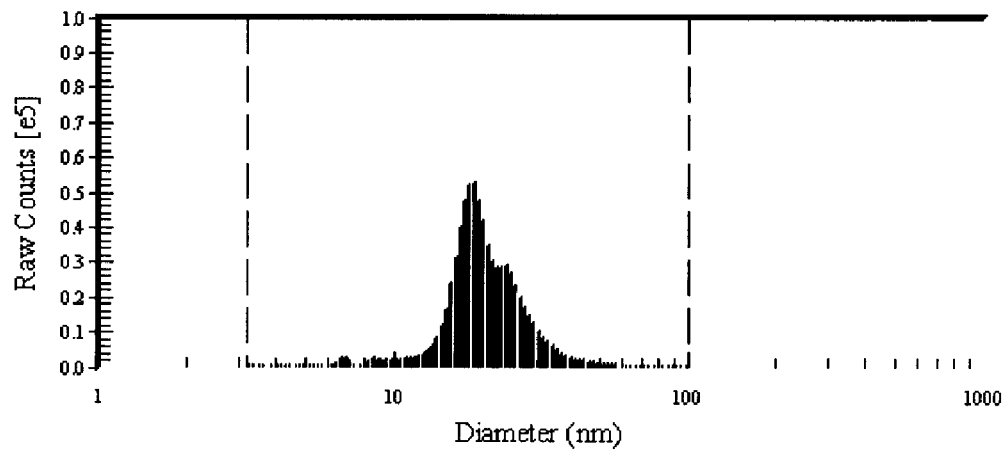
FIG. 6 is a curve diagram illustrating the particle size distribution of 4 mg/mL BSA solution dissolved into 0.2 M $CH_3COONH_4$ (ammonium acetate)
Figure 7:
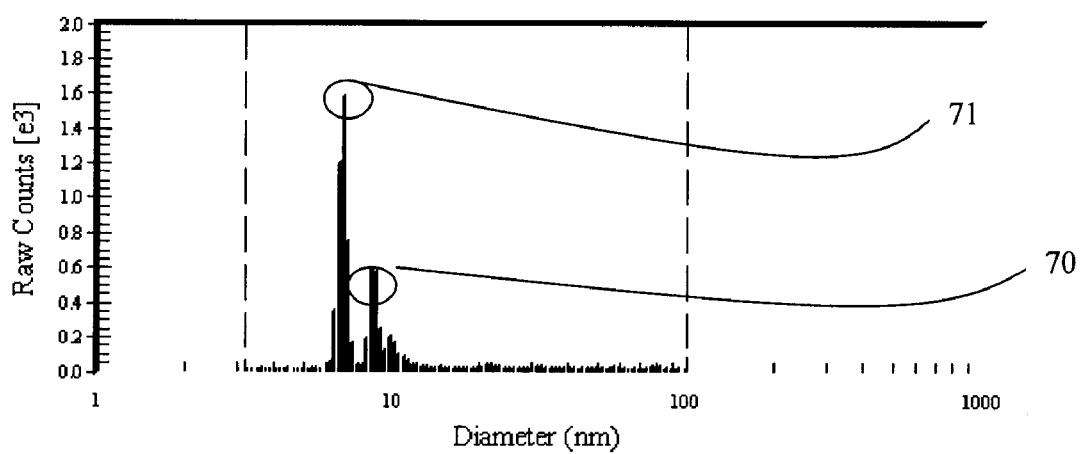
FIG. 7 is a curve diagram illustrating the particle size distribution of 0.02 mg/mL BSA solution dissolved into 0.2 M $CH_3COONH_4$ (ammonium acetate)

The test results executed by the apparatus and the system are shown in FIGS. 6 and 7 since the BSA (bovine serum albumin) solution is taken as an example. After the BSA solution with the concentration 4 mg/mL passes through the sieve (particle size) and the particle counter, the average particle size of the BSA is 19 nm. If the concentration is decreased to the 0.02 mg/mL, the average particle size is about 6.9 nm as shown in FIG. 7. The error between the 6.9 nm (the most abundant peak) and the theoretical value (6.5 nm) can be decreased to 6%. As shown in FIG. 7, a signal 70 of 8.5 nm may exist, besides obvious peak 71 of 6.5 nm. It supposes that the same protein affects the size of the nano-particles due to the change of the three-dimensional conformation. The misgiving of influencing the particle size resulting from the piping delivery can be initially eliminated through the test results. Secondly, for the surfaces of the some materials carrying charges, the concentration should be especially decreased to prevent the measured data of the particle size from being estimated highly.

Furthermore, the nano-particles can be selected from organic nano-particles, inorganic nano-particles or other type of nano-particles. The nano-particles include metal and/or metal oxide nanoparticles, polymer nano-particles and macromolecules. The metal or metal oxide nanoparticles can be preferably Aurum and titania. The polymer nano-particles can be preferably polystyrene beads and polystyrene latex. The macromolecule can be preferably protein, DNA (deoxyribonucleic acid), RNA (ribonucleic acid) or polysaccharide.

Figure 8:
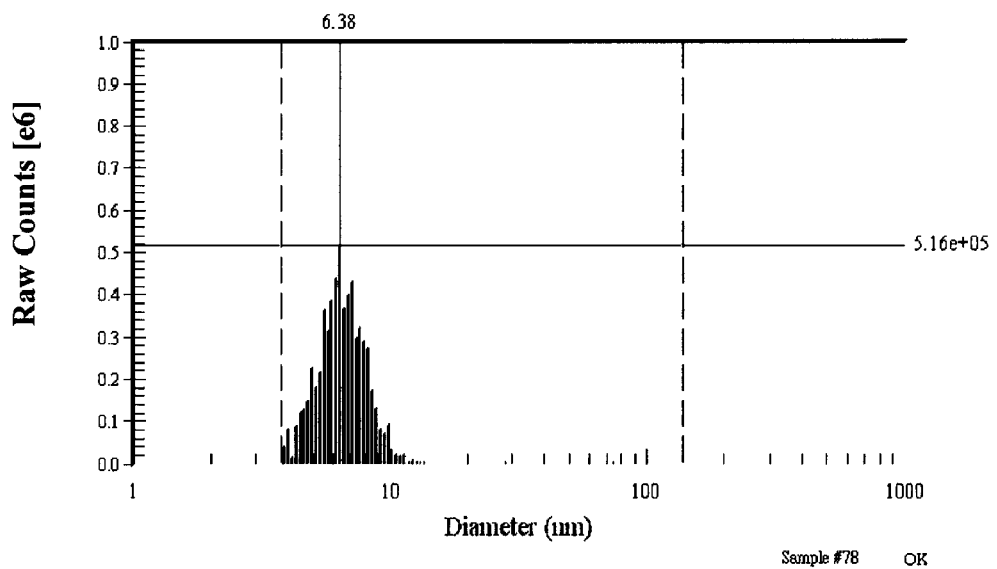
FIG. 8 is a curve diagram illustrating GNP (gold nano-particle) applied to the apparatus and the system of the present invention.
Figure 9:
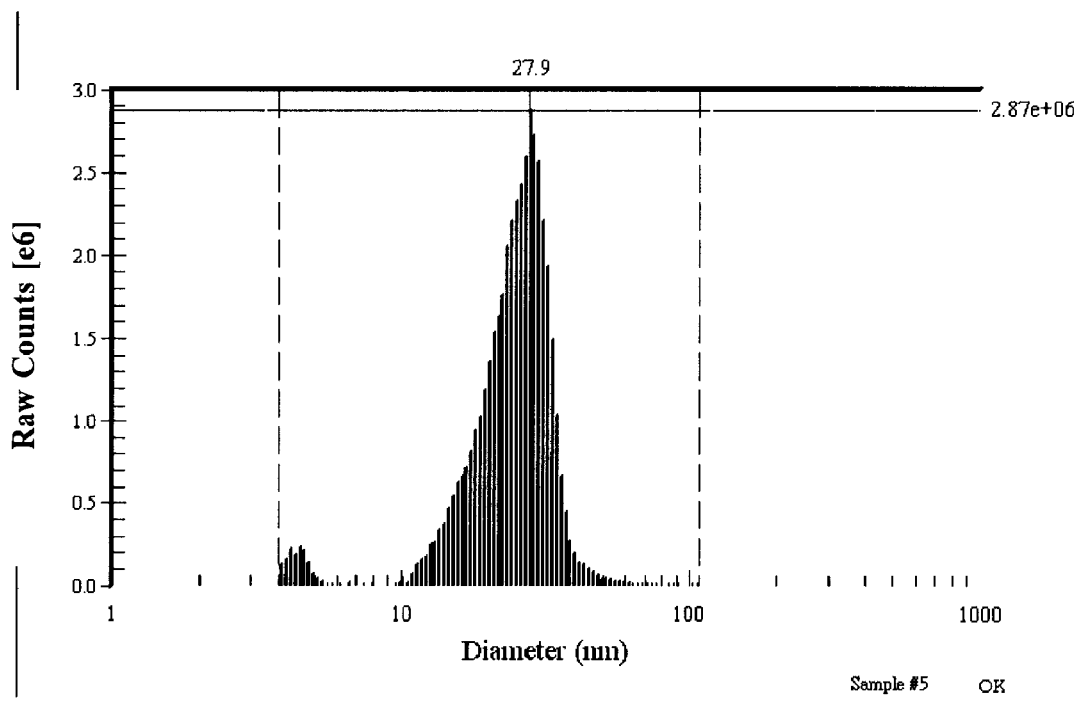
FIG. 9 is a curve diagram illustrating polystyrene beads applied to the apparatus and the system of the present invention.
Figure 10:
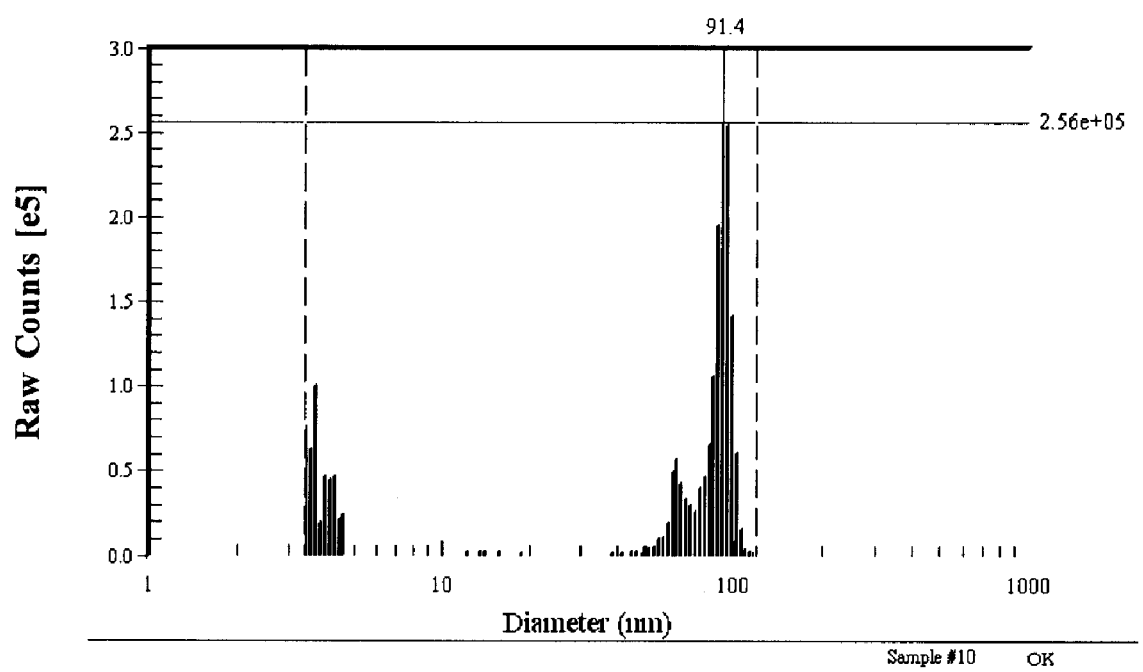
FIG. 10 is a curve diagram illustrating polystyrene latex applied to the apparatus and the system of the present invention.

Referring to FIGS. 8-10 for other test results executed by the apparatus and the system of the present invention are illustrated. FIG. 8 is a curve diagram illustrating GNP (gold nano-particle) applied to the apparatus and the system. The measured particle size of the GNP is about 6.44±1.24 nm by comparing with the 5 nm of the theoretical value. FIG. 9 is a curve diagram illustrating polystyrene beads applied to the apparatus and the system. The measured particle size of the polystyrene bead is about 25.3±1.5 nm by comparing with the 24.0±4.0 nm of the theoretical value. FIG. 10 is a curve diagram illustrating polystyrene latex applied to the apparatus and the system. The measured particle size of the polystyrene latex is about 85.5±3.67 nm by comparing with the 90 nm of the theoretical value.

Although the features and advantages of the embodiments according to the preferred invention are disclosed, it is not limited to the embodiments described above, but encompasses any and all modifications and changes within the spirit and scope of the following claims.

TABLE 1

| Instrument name | specification |
|---|---|
| | Hardware |
| Nano-particle detection system | 1. Nanosuspension particle counter<br>(1) particle size range: the minimum ($D_{50}$): 2.5 nm, the maximum: >3 μm<br>(2) concentration range: 0~3 × $10^5$ particles/$cm^3$<br>(3) concentration precision: <±10%<br>(4) background interference signal: must <0.01 particles/$cm^3$<br>(5) reaction time: <0.8 second in the high flow mode, <5 second in the low flow mode<br>(6) average interval: panel setting<br>(7) analog input: at least two BNC junctions, from 0 to 10 V<br>(8) output: digital display, concentration time, concentration, time and total numbers of particles, status<br>2. Sieve for nanosuspension particles<br>(1) operation mode: charge neutralization for bipolar<br>(2) particle type: apply to a solid or a non-volatile liquid<br>(3) sieving range: 2~150 nm<br>(4) maximum injection concentration: 10 nm, at least $10^8$ particles/cm<br>3. Aerosol generator for nanosuspension particles<br>(1) generation rate for aerosol particles: >$10^7$ partilces/$cm^3$<br>(2) aerosol particle size range: from 3 to 100 nm<br>(3) pressure difference: from 0 to 5 psi (average 3 psi)<br>(4) air flow: from 0.2 to 2.5 L/min<br>(5) $CO_2$ flow = from 0.05 to 0.5 L/min<br>4. Atomizer<br>(1) average particle size for drops: DOP - 0.3 μm, water - 0.35 μm<br>(2) concentration: >$10^6$ particles/cc<br>(3) material: PSL, DOP, DEHS, oil, water or alcohol solution or suspension<br>(4) maximum PSL particle size: 2 μm<br>(5) nozzle flow: 3.0-3.5 L/min<br>(6) liquid flow: 20 $cm^3$/min<br>5. Containing apparatus<br>(1) include a containing device<br>(2) gas flow: 0-50 liter*1, 0-20 liter*2, 0-5 liter*4<br>(3) oxygen analyzer:<br>a. operation temperature: >770° C.<br>b. oxygen sensor range: dynamic range 20 orders<br>c. reaction speed: <50 seconds from 10 PPM to 1*$10^{-5}$ PPM<br>d. principle: solid electrolyte ceramic (ZrO2) sensor<br>(4) must measure temperature, humidity, pressure<br>(5) must equip with an alarm system for |

TABLE 1-continued

| Instrument name | specification |
|---|---|
| | insufficient pressure<br>(6) must equip with a device for producing different air stream<br>(7) must connect with the hardware specification from 1-4 |
| | Software specification |
| | (1) 32-bit design for Windows Operating system<br>(2) include various data display formats such as tables and figures<br>(3) display channel and original data<br>(4) high resolution display, every decimal from 4 to 64 channels<br>(5) data can be computed based on numbers, areas or volumes<br>(6) data file can be outputted to the trial balance or other application software for further processing<br>(7) multiple scan average<br>(8) buffer area can provide two data set for subtraction or comparison<br>(9) correction<br>(10) interval time for sampling and start/end time setting<br>(2) automatic file saving and printing |
| | Auxiliary equipment |
| | 1. computer, LCD 17 inch, black and white laser printer<br>2. gas proof casing for experiment *2<br>3. must equip with piping that includes samples, gas inlets, and measuring instruments |

What is claimed is:

1. A nano-particle containing apparatus comprising:

a casing having a containing space for accommodating a plurality of nano-particles;

an air extracting device for pumping the nano-particles from the containing space;

a pressure control device for controlling the pressure status of the containing space; and a measuring instrument for detecting the status of an object affected by the nano-particles after the object is delivered into the containing space.

2. The nano-particle containing apparatus of claim 1, wherein an internal wall surface of the casing has active self-cleaning function.

3. The nano-particle containing apparatus of claim 2, wherein the internal wall surface of the casing can dispose a conductive thin film for executing active self-cleaning function.

4. The nano-particle containing apparatus of claim 1, wherein the air extracting device is a pump.

5. The nano-particle containing apparatus of claim 1, wherein the measuring instrument further includes a temperature monitoring device for monitoring and reading the temperature of the containing space.

6. The nano-particle containing apparatus of claim 1, wherein the measuring instrument further includes a humidity monitoring device for monitoring and reading the humidity of the containing space.

7. The nano-particle containing apparatus of claim 1, wherein the measuring instrument further includes a carbon dioxide monitoring device for monitoring and reading the concentration of carbon dioxide in the containing space.

8. A nano-particle detection system, comprising:

a generating device for generating a plurality of nano-particles;

a containing apparatus comprising a casing having a containing space that allows the nano-particles to be uniformly distributed therein and an internal wall surface of the casing having active self-cleaning function, an air extracting device for pumping the nano-particles from the containing space, a pressure control device for controlling the pressure status of the containing space, and a measuring instrument;

an analyzer for analyzing particle sizes of the nano-particles within the containing space; and a detector for detecting a concentration of the nano-particles within the containing space, wherein an object is placed into the containing space to allow the object to be exposed to the nano-particles, and the effect degree of the object exposed to the nano-particles is detected by the measuring instrument after achieving a predetermined time.

9. The nano-particle detection system of claim 8, wherein the generating device is an electronic spray device.

10. The nano-particle detection system of claim 8, wherein the generating device is pneumatic and spray equipment.

11. The nano-particle detection system of claim 8, wherein the nano-particles attached to the internal wall surface are removed into the containing space through self-cleaning function, and the nano-particles are pumped by the air extracting device from the containing space, so that the containing device can be repeatedly used.

12. The nano-particle detection system m of claim 11, wherein the internal wall surface can dispose a conductive thin film for executing active self-cleaning function.

13. The nano-particle detection system of claim 8, wherein the air extracting device is a pump.

14. The nano-particle detection system of claim 8, wherein the containing apparatus is further equipped with a temperature monitoring device for monitoring and reading the temperature of the containing space.

15. The nano-particle detection system of claim 8, wherein the containing apparatus is further equipped with a humidity monitoring device for monitoring and reading the humidity of the containing space.

16. The nano-particle detection system of claim 8, wherein the containing apparatus is further equipped with a carbon dioxide monitoring device for monitoring and reading the concentration of carbon dioxide in the containing space.

17. The nano-particle detection system of claim 8, wherein the object is a biological specimen.

18. A method for detecting safety of nano-particles, the method comprising the following steps:

providing a casing having a containing space to place an object;

injecting a plurality of nano-particles into the containing space to allow the nano-particles to be uniformly distributed inside the containing space;

controlling a pressure status of the containing space by a pressure control device;

detecting a status of an object affected by the nano-particles by a measuring instrument after achieving a predetermined time; and pumping the nano-particles from the containing space by an air extracting device.

19. The method for detecting safety of nano-particles of claim 18, further comprising the step of monitoring and controlling the temperature status, the humidity status and the concentration of carbon dioxide.

20. The method for detecting safety of nano-particles of claim 18, further comprising the step of providing a biological specimen as the object.

* * * * *